United States Patent
Antila et al.

(10) Patent No.: US 6,506,897 B1
(45) Date of Patent: Jan. 14, 2003

(54) METHOD OF PREPARING L-ARABINOSE FROM SUGAR BEET PULP

(75) Inventors: Juhani Antila, Espoo (FI); Vili Ravanko, Kirkkonummi (FI); Pertti Walliander, Kantvik (FI)

(73) Assignee: Danisco Finland Oy, Espoo (FI)

( * ) Notice: Subject to any disclaimer, the term of this patent is extended or adjusted under 35 U.S.C. 154(b) by 0 days.

(21) Appl. No.: 09/486,437

(22) PCT Filed: Aug. 26, 1998

(86) PCT No.: PCT/FI98/00667

§ 371 (c)(1),
(2), (4) Date: Oct. 30, 2000

(87) PCT Pub. No.: WO99/10542

PCT Pub. Date: Mar. 4, 1999

(30) Foreign Application Priority Data

Aug. 26, 1997 (FI) .................................................. 973501
Jan. 20, 1998 (FI) .................................................. 980119

(51) Int. Cl.⁷ ................................................ C07H 1/08
(52) U.S. Cl. ..................................................... 536/128
(58) Field of Search ........................................ 536/128

(56) References Cited

U.S. PATENT DOCUMENTS 4,816,078 A 3/1989 Schiweck et al.

FOREIGN PATENT DOCUMENTS

| DE | 1 43 261 | 8/1980 |
| GB | 1182099 | 2/1970 |
| WO | WO 97/30215 | 8/1997 |

OTHER PUBLICATIONS

Chemical Abstracts vol. 97 (1982), 90747d.
Chemical Abstracts vol. 98 (1983), 33388j.

*Primary Examiner*—Raymond Henley, III
(74) *Attorney, Agent, or Firm*—Nixon & Vanderhye

(57) ABSTRACT

The invention relates to a method of preparing crystalline L-arabinose by extraction of sugar beet pulp, from which sugar has been extracted, in a strong alkaline solution, by hydrolysis of the obtained crude araban with a strong acid at an elevated temperature, by neutralization and filtration of the obtained solution, by chromatographic separation of the L-arabinose fraction, by purification of the obtained L-arabinose solution by means of cation and anion exchangers and adsorbent resins, and by recovering the pure L-arabinose as a crystalline product.

10 Claims, No Drawings

METHOD OF PREPARING L-ARABINOSE FROM SUGAR BEET PULP

This is a 317 of PCT/FI98/00667 filed Aug. 26, 1998.

The invention relates to a method of preparing crystalline L-arabinose by extraction of sugar beet pulp, from which sugar has been extracted, in a strong alkaline solution, by hydrolysis of the obtained crude araban with a strong acid at an elevated temperature, by chromatographic separation of the L-arabinose fraction, by purification of the obtained L-arabinose solution by means of cation and anion exchangers and adsorbent resins, and by recovering the pure L-arabinose as a crystalline product.

DESCRIPTION OF THE PRIOR ART

L-arabinose has been prepared by acid hydrolysis from arabinose-containing vegetable materials, such as gum arabic. Another well known raw material is sugar beet pulp from which sugar has been extracted; L-arabinose has been prepared from this material by alkaline or acid hydrolysis followed by multistep purification. U.S. Pat. No. 4,816,078, for example, teaches a method of preparing L-arabinose from sugar beet pulp by hydrolysis in the presence of lime, by filtration and chromatographic separation of the araban fraction; whereupon the araban is subjected to hydrolysis by addition of acid, and the obtained L-arabinose is separated by chromatography using a cation exchanger in Ca-form. According to a previous method described in GB published application 1,182,099, L-arabinose is prepared from a beet pulp hydrolyzate by crystallization from an alcoholic solution.

BRIEF DESCRIPTION OF THE INVENTION

It has now been discovered that L-arabinose can be obtained with good yield from sugar beet pulp, from which sugar has been extracted, by simple alkaline extraction, by acid hydrolysis and chromatographic separation using as separating resin a cation exchanger in monovalent metal ($Na^+$) form, to obtain an L-arabinose-containing fraction. As a last step, the L-arabinose is crystallized from an aqueous solution. The method avoids the previous multiple separation and purification steps.

DETAILED DESCRIPTION OF THE INVENTION

The method of the invention enables the preparation of pure L-arabinose. In accordance with the invention, sugar beet pulp, from which sugar has been extracted, is extracted with an alkaline solution to dissolve the araban. After filtration the alkaline extract is hydrolyzed with acid to obtain a crude L-arabinose solution. The crude arabinose fraction is subjected to chromatographic separation by using a cation exchanger resin in monovalent metal ($Na^+$) form (e.g. sulphonated polystyrenedivinyl benzene; 5.5% DVB) and water as eluent. The solution is then purified by ion exchange. The solution is concentrated to about 70 percent by weight, and the pure L-arabinose is crystallized. The crystals are separated by centrifugation and dried in air.

The separating resin used in the chromatographic separation is preferably sulphonated polystyrenedivinyl benzene (5.5% DVB) in monovalent metal ($Na^+$, $K^+$) form. Purification and colour removal is carried out with cation and anion exchange resins and other adsorption resins.

As feedstock is preferably used sugar beet pulp stabilized by the biotechnical method according to Finnish Patent Application 973,501. The following presents a general flow chart.

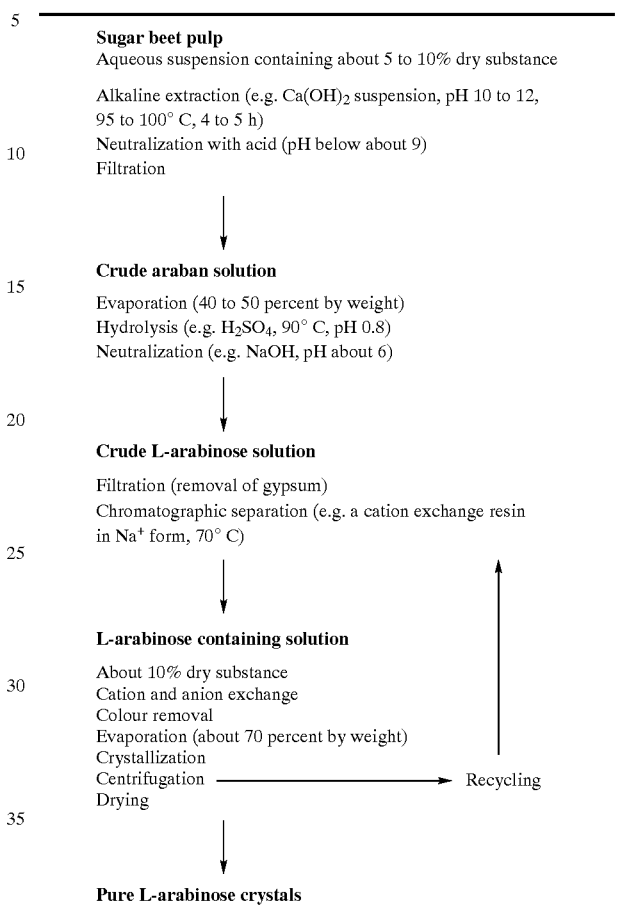

PREFERRED EMBODIMENT OF THE INVENTION

In accordance with a preferred embodiment of the invention, sugar beet pulp, from which sugar has been extracted, is suspended in a strong alkaline solution and extracted for 4 to 5 hours at a pH of about 10 to 12 and a temperature of 95 to 100° C. The alkaline "solution" is preferably milk of lime containing 25 to 40 percent by weight of $Ca(OH)_2$ calculated on the dry substance of the sugar beet pulp. Optionally, buffered alkaline solutions (KOH, NaOH) can be used in the extraction. The obtained mixture is neutralized with e.g. carbon dioxide or optionally sulphuric acid to about pH 9 or below to precipitate the calcium salt. After filtration the solution is concentrated to about 40 percent by weight and then subjected to acid hydrolysis, e.g. by addition of sulphuric acid, to pH about 0.8. The hydrolysis is carried out at about 90° C., whereupon the solution is cooled to about 70° C. and neutralized by addition of an alkali (e.g. NaOH) to pH about 6. The neutralized solution is subjected to chromatographic separation by using a cation exchange resin in monovalent metal form, preferably $Na^+$ form. The separated arabinose-containing fraction has a dry substance content of 5 to 10%, of which 75 to 80% is L-arabinose. Pure L-arabinose crystals are obtained by evaporation (a solution of about 70 percent by weight), seeding and cooling crystallization. The crystals can be separated by centrifugation.

Another preferable way to extract and hydrolyze araban is to continue by acid hydrolysis after alkaline hydrolysis to degrade the araban into L-arabinose. In this embodiment the alkaline extraction takes about 4 to 5 hours, whereupon the pH is adjusted to about 0.8 with sulphuric acid. The extract is treated at 90° C. until the araban is degraded, whereupon the suspension is neutralized (pH 6), filtered by a filter press and concentrated by evaporation for chromatographic separation.

The choice of embodiment depends on equipment capacity and the suitability of the raw material.

EXAMPLE 1

Calcium hydroxide in an amount of 30 to 40 percent by weight was added to hot water (95 to 100° C.). Dried sugar beet pulp, from which sugar had been extracted and which had a coarseness of about 0.5 cm, was suspended in the obtained milk of lime to a solution of about 8 percent by weight, and mixed for 3 to 4 hours at a temperature of 95 to 100° C. and a pH of 10 to 12. The mixture was cooled to 75° C. and neutralized by addition of carbon dioxide to pH 9 to precipitate the calcium carbonate. The neutralized mixture was filtered in a filter press.

The filtrate which contained 4% of polysaccharides (crude arabinogalactan) was concentrated to 40 percent by weight by evaporation and sulphuric acid was added to pH 0.8. The araban was hydrolyzed at 90° C., whereupon the solution was cooled to 70° C. and 10 percent by weight sodium hydroxide solution was added to pH 6. The neutralized solution was filtered and the L-arabinose separated by chromatography by using a sulphonated polystyrenedivinyl benzene cation exchange resin in $Na^+$ form. An L-arabinose fraction containing 8% of dry substance (of which 80% was L-arabinose) was recovered. The L-arabinose solution was concentrated to 30 percent by weight by evaporation and purified by cation and anion exchange followed by colour removal with Optipore® (Dovex®) adsorption resin (manufacturer Dow Chemicals, USA). The purified solution was concentrated to 70 percent by weight, seeded with arabinose crystals and allowed to crystallize by cooling to room temperature. The crystals (arabinose purity over 98%) were separated by centrifugation and dried in a hot air current. The yield of L-arabinose crystals was 10 percent by weight of the pulp dry substance.

EXAMPLE 2

Fresh sugar beet pulp, from which sugar had been extracted and which had a coarseness of about 0.5 cm and which had been pre-treated with biotechnical pre-treatment (described in Patent Application 973,501 and in Example 3), was suspended into hot (95 to 100° C.) milk of lime (30 to 40% $Ca(OH)_2$ of the beet pulp dry substance) to a mixture of 7 percent by weight. The mixture was extracted as in Example 1, the extracted pulp was separated from the solution by a decanting centrifuge and the crude araban was hydrolyzed as in Example 1. The L-arabinose was separated by chromatography and purified by ion exchange and colour was removed as in Example 1. The L-arabinose was crystallized from the concentrated solution with a yield of 15% of the pulp dry substance.

EXAMPLE 3

Fresh sugar beet pulp, from which sugar had been extracted and which had a coarseness of about 0.5 cm and which had been pre-treated with biotechnical pretreatment (described in Finnish Patent Application 973,501 and in Example 3), was suspended into hot (95 to 100° C.) milk of lime (30 to 40% $Ca(OH)_2$ of the beet pulp dry substance) to a mixture of 7 percent by weight. The mixture was extracted as in Example 1, the extracted pulp was separated from the solution by a decanting centrifuge and the crude araban was hydrolyzed as in Example 1. The L-arabinose was separated by chromatography and purified by ion exchange and colour was removed as in Example 1. The L-arabinose was crystallized from the concentrated solution with a yield of 15% of the pulp dry substance.

EXAMPLE 4

The crude arabinose solution obtained from acid hydrolysis was filtered and subjected to chromatographic separation to purify L-arabinose from other components.

The separation was performed in a pilot chromatographic column as a batch process. A cation exchange resin (manufacturer Finex Oy, Finland) in $Na^+$ form was used. The resin was sulphonated polystyrene which was cross-linked with divinyl benzene; the cross-linkage degree of the resin was 5.5% and average particle size 0.35 mm. The inner diameter of the column was 1.0 m and the height of the resin bed was about 5.2 m, resulting in a resin volume of about 4,000 liters. The separation was carried out at 80° C. (a heated column was used) with ion exchanged water as eluent.

The separation process was carried out as follows:

Step 1:

About 400 liters of arabinose solution (125 kg dry substance) was applied to the column through a heat exchanger using a flow rate of about 750 l/h. The dry substance content of the solution was about 35 g dry substance in 100 g solution.

Step 2:

The eluent (ion exchanged water) was led downwards in the column using a flow rate of 650 l/h. The eluent was also applied through the heat exchanger.

Step 3:

The density and conductivity of the solution discharged from the column was measured and recorded continuously. According to this information, the solution was divided into two fractions: a residual fraction (containing salts and small amounts of glucose, galactose and fructose) and an arabinose fraction (containing arabinose and small amounts of galactose and fructose).

A recycle fraction containing glucose, galactose, fructose and a small amount of arabinose can also be recovered between the two fractions.

The recycle fraction can be reapplied into the column or used for diluting the feed solution.

The amounts of dry substance (DS) and the compositions of the arabinose fraction and the feed solution are presented in Table 1. The concentrations of the components are expressed as percent by weight of the total dry substance of the fraction. The yield expresses the amount of L-arabinose in the arabinose fraction in relation to the total amount of L-arabinose calculated on the basis of the amounts of L-arabinose in both obtained fractions.

TABLE 1

Values and compositions of feed solution and arabinose fraction, and L-arabinose yield

|  | Feed solution | Arabinose fraction |
| --- | --- | --- |
| DS in fraction, kg | 127.8 | 39.2 |
| DS, g/100 g solution | 35.5 | 9.8 |
| Conductivity, mS/cm | 30.9 | 1.4 |
| pH | 5.1 | 4.7 |
| Glucose, % of DS | 1.8 | 0.7 |
| Galactose, % of DS | 1.3 | 2.1 |
| Fructose, % of DS | 1.2 | 2.9 |
| Arabinose, % of DS | 24.7 | 77.6 |
| Arabinose yield, % |  | 96.3 |

Arabinose yield is the relation of the amount of arabinose in the arabinose fraction to the amount of arabinose in the feed solution (%).

EXAMPLE 5

Crude arabinose solution obtained from acid hydrolysis was filtered with a pressure filter and fractionated by chromatography in plant scale. The separating column employed was a conventional batch separation column, height 7.0 m and inner diameter 2.8 m.

The separation resin used was a cation exchange resin in $Na^+$ form (manufacturer Finex Oy, Finland). The resin was sulphonated polystyrene cross-linked with divinyl benzene; cross-linkage degree was 5.5% and particle size about 0.45 mm. The height of the resin bed was about 6.4 m and the resin volume was consequently about 38 $m^3$. The temperature in the column and the feed solution tank was about 70° C.

The principle of the separation is the same as in Example 1 (steps 1 to 3). Feed size was about 2,000 liters (780 kg dry substance), i.e. the concentration was 34 g in 100 g of solution. Flow rate in the column was about 5 $m^3/h$. Two fractions were recovered as in Example 1. Table 2 shows the dry substance (DS) contents and compositions of the feed solution and the arabinose fraction.

TABLE 2

Values and compositions of feed solution and arabinose fraction, and L-arabinose yield

|  | Feed solution | Arabinose fraction |
| --- | --- | --- |
| DS in fraction, kg | 777 | 157 |
| DS, g/100 g solution | 33.9 | 5.6 |
| pH | ~6 | ~5 |
| Glucose, % of DS | 1.7 | 0.5 |
| Galactose, % of DS | 2.4 | 3.5 |
| Fructose, % of DS | 1.2 | 3.1 |
| Arabinose, % of DS | 18.0 | 80.5 |
| Arabinose yield, % |  | 90.4 |

The yield was calculated as in the previous example.

EXAMPLE 6

Calcium hydroxide in an amount of 40 percent by weight calculated on the dry substance of the beet pulp to be treated was added to hot water at about 98° C. The dry, almost sugarless pulp was suspended in an alkaline solution to a mixture of about 9 percent by weight, and the mixture was mixed for 4 hours at a temperature of 98° C. and a pH of about 10. Sulphuric acid was then added to the mixture to pH 0.8 and the araban was hydrolyzed into L-arabinose at a temperature of 90° C. The suspension was cooled to 70° C. and 10 percent by weight sodium hydroxide solution was added to pH 6.0. The neutralized mixture was filtered by a filter press and concentrated to 40 percent by weight.

The solution was fine-filtered by a Seitz filter by means of siliceous earth, whereupon the L-arabinose was separated from the solution by chromatography as in the previous examples. An L-arabinose fraction having a dry substance content of 8 percent by weight, of which 80% was L-arabinose, was recovered. The solution was concentrated by evaporation to 30 percent by weight, purified by cation and anion exchange and by colour removal resin (Optipore®/Dovex®), and evaporated to 70 percent by weight. The solution was then seeded and the L-arabinose crystallized by cooling the solution to room temperature. The purity of the crystals exceeded 98%. The arabinose yield was 10% calculated on the dry substance of the raw material.

What is claimed is:

1. A method of preparing crystalline L-arabinose, characterized by the combination of the following steps:
    a) extraction of sugar beet pulp, from which sugar has been extracted, in a strong alkaline solution,
    b) hydrolysis of the obtained crude araban with a strong acid at an elevated temperature,
    c) neutralization and filtration of the obtained solution,
    d) chromatographic separation of the L-arabinose fraction by using a cation exchanger in monovalent metal form as separation resin,
    e) purification of the obtained L-arabinose solution by means of cation and anion exchangers and adsorbent resins, and
    f) recovery of the pure L-arabinose as a crystalline product.
2. A method as claimed in claim 1, characterized in that in step a) the extraction is carried out at pH 10 to 12.
3. A method as claimed in claim 2, characterized in that a calcium hydroxide suspension is used as the alkali.
4. A method as claimed in claim 1, characterized in that in step c) pH is 6 at the end of neutralization.
5. A method as claimed in claim 4, characterized in that neutralization is carried out with carbon dioxide or sulphuric acid.
6. A method as claimed in claim 1, characterized in that in step b) the hydrolysis is carried out at a pH of about 0.8 at a temperature of about 90° C.
7. A method as claimed in claim 1, characterized in that in step d) the cation exchanger is in $Na^+$ form.
8. A method as claimed in claim 1, characterized in that in step a) the sugar beet pulp is sugar beet pulp stabilized by a biotechnical method.
9. A method as claimed in claim 8, characterized in that the pH of the stabilized sugar beet pulp is 3.5 to 4.5 and the dry substance content 20 to 27 percent by weight, and the pulp is substantially free from fermentable sugars.
10. A method as claimed in claim 9 wherein said pH is 3.9 to 4.3.

* * * * *

UNITED STATES PATENT AND TRADEMARK OFFICE
CERTIFICATE OF CORRECTION

PATENT NO. : 6,506,897 B1 Page 1 of 1
DATED : January 14, 2003
INVENTOR(S) : Antila et al.

It is certified that error appears in the above-identified patent and that said Letters Patent is hereby corrected as shown below:

Title page,
Item [73], Assignee, "[73] Assignee:    Danisco Finland Oy, Espoo (FI)" to read as
-- [73]   Assignee:    Danisco Sugar Finland Oy, Espoo (FI) --

Signed and Sealed this

First Day of April, 2003

JAMES E. ROGAN
*Director of the United States Patent and Trademark Office*